(12) United States Patent
Parker et al.

(10) Patent No.: US 7,517,701 B2
(45) Date of Patent: *Apr. 14, 2009

(54) LUMINESCENT LANTHANIDE COMPLEXES

(75) Inventors: David Parker, Durham (GB); Paul Atkinson, Stockton-on-Tees (GB); Filip Kielar, Bruntal (CZ); Annegret Boge, San Jose, CA (US); J. Richard Sportsman, Encinitas, CA (US); Elizabeth Gaudet, Menlo Park, CA (US); George G. Yi, Sunnyvale, CA (US)

(73) Assignee: MDS Analytical Technologies (US) Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/250,722

(22) Filed: Oct. 14, 2005

(65) Prior Publication Data

US 2007/0087452 A1 Apr. 19, 2007

Related U.S. Application Data

(63) Continuation of application No. PCT/US2005/035215, filed on Sep. 30, 2005.

(60) Provisional application No. 60/683,377, filed on May 20, 2005, provisional application No. 60/615,308, filed on Sep. 30, 2004.

(51) Int. Cl.
*G01N 33/535* (2006.01)
*G01N 33/532* (2006.01)
*G01N 33/24* (2006.01)
*G01N 21/76* (2006.01)
*G01N 33/53* (2006.01)
*A61K 51/06* (2006.01)

(52) U.S. Cl. .............. 436/546; 435/7.5; 436/172; 436/544; 436/56; 436/81; 530/391.5; 534/10; 534/15; 534/16

(58) Field of Classification Search ............ 534/10, 534/15, 16; 436/546, 172, 544, 56, 81; 435/6, 435/7.5, 188; 530/391.5
See application file for complete search history.

(56) References Cited

U.S. PATENT DOCUMENTS

| | | |
|---|---|---|
| 3,135,793 A | 6/1964 | William |
| 3,214,377 A | 10/1965 | Hotten |
| 3,485,818 A | 12/1969 | Thompson |
| 4,181,654 A | 1/1980 | Weitl et al. |
| 4,341,957 A | 7/1982 | Weider |
| 4,374,120 A | 2/1983 | Soini et al. |
| 4,421,654 A | 12/1983 | Plueddemann |
| 4,565,790 A | 1/1986 | Hemmila et al. |
| 4,587,223 A | 5/1986 | Soini et al. |
| 4,637,988 A | 1/1987 | Hinshaw et al. |
| 4,724,217 A | 2/1988 | Miller |
| 4,761,481 A | 8/1988 | Hale et al. |
| 4,794,191 A | 12/1988 | Hinshaw et al. |
| 4,801,722 A | 1/1989 | Hinshaw et al. |
| 4,808,541 A | 2/1989 | Mikola et al. |
| 4,837,169 A | 6/1989 | Toner |
| 4,885,363 A | 12/1989 | Tweedle et al. |
| 4,920,195 A | 4/1990 | Kankare et al. |
| 4,966,917 A | 10/1990 | White |
| 5,021,567 A | 6/1991 | Johnson et al. |
| 5,032,677 A | 7/1991 | Hale et al. |
| 5,039,512 A | 8/1991 | Kraft et al. |
| 5,055,578 A | 10/1991 | Hale et al. |
| 5,077,037 A | 12/1991 | Wallace |
| 5,106,957 A | 4/1992 | Hale et al. |
| 5,116,989 A | 5/1992 | Hale et al. |
| 5,160,957 A | 11/1992 | Ina et al. |
| 5,202,423 A | 4/1993 | Kankare et al. |
| 5,216,134 A | 6/1993 | Mukkala et al. |
| 5,219,553 A | 6/1993 | Kraft et al. |
| 5,232,858 A | 8/1993 | Wolfbeis et al. |
| 5,245,038 A | 9/1993 | Hale et al. |
| 5,252,462 A | 10/1993 | Drevin et al. |
| 5,252,740 A | 10/1993 | Hale et al. |
| 5,256,535 A | 10/1993 | Ylikoski et al. |
| 5,271,929 A | 12/1993 | Hashiguchi et al. |
| 5,281,704 A | 1/1994 | Love et al. |

(Continued)

OTHER PUBLICATIONS

Y. Bretonniere et al, Chemical Communications [Cambridge UK] (2002), vol. 17, pp. 1930-1931.*

(Continued)

*Primary Examiner*—Mark L. Shibuya
*Assistant Examiner*—Shafiqul Haq
(74) *Attorney, Agent, or Firm*—Kolisch Hartwell, PC

(57) ABSTRACT

Systems, including compositions, kits, and methods, particularly for photoluminescence applications. The systems may include, among others, (1) organic chelators, (2) complexes between the chelators and lanthanide ions, and (3) precursors, derivatives, and uses thereof. The chelators may include a 1,4,7,10-tetraazacyclododecane ring system, for example, having the formula:

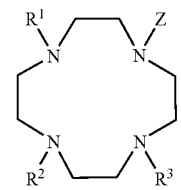

Here, $R^1$, $R^2$, and $R^3$ are substituents of the tetraazacyclododecane ring system, that is further substituted at the 10-position by a sensitizer Z that is typically a polyheterocyclic ring system. The organic chelator may be capable of forming a luminescent complex with a lanthanide ion, and is optionally further substituted by a reactive functional group or a conjugated substance. The resulting lanthanide complex may be useful in luminescence-based assays, such as energy transfer assays, among others.

26 Claims, No Drawings

U.S. PATENT DOCUMENTS

| | | | |
|---|---|---|---|
| 5,312,986 A | 5/1994 | Simon et al. |
| 5,316,757 A | 5/1994 | Sherry et al. |
| 5,316,909 A | 5/1994 | Xu |
| 5,324,825 A | 6/1994 | Kankare et al. |
| 5,364,613 A | 11/1994 | Sieving et al. |
| 5,369,108 A | 11/1994 | Breslow et al. |
| 5,428,154 A | 6/1995 | Gansow et al. |
| 5,446,145 A | 8/1995 | Love et al. |
| 5,457,186 A | 10/1995 | Mukkala et al. |
| 5,462,725 A | 10/1995 | Kiefer et al. |
| 5,464,607 A | 11/1995 | Anelli et al. |
| 5,482,699 A | 1/1996 | Almen et al. |
| 5,512,493 A | 4/1996 | Mathis et al. |
| 5,527,684 A | 6/1996 | Mabile et al. |
| 5,531,978 A | 7/1996 | Berg et al. |
| 5,554,749 A | 9/1996 | Wallace et al. |
| 5,561,052 A | 10/1996 | Koike |
| 5,571,897 A | 11/1996 | Takalo et al. |
| 5,573,752 A | 11/1996 | Ranganathan et al. |
| 5,583,219 A | 12/1996 | Subramanian et al. |
| 5,616,312 A | 4/1997 | Rosik |
| 5,622,821 A | 4/1997 | Selvin et al. |
| 5,637,509 A | 6/1997 | Hemmila et al. |
| 5,639,615 A | 6/1997 | Selvin et al. |
| 5,656,254 A | 8/1997 | Ramalingam et al. |
| 5,656,433 A | 8/1997 | Selvin et al. |
| 5,712,389 A | 1/1998 | Meyer et al. |
| 5,731,147 A | 3/1998 | Bard et al. |
| 5,736,410 A | 4/1998 | Zarling et al. |
| 5,762,910 A | 6/1998 | Unger et al. |
| 5,827,653 A | 10/1998 | Sammes et al. |
| 5,830,769 A | 11/1998 | Wieder et al. |
| 5,849,794 A | 12/1998 | Bianchi et al. |
| 5,853,699 A | 12/1998 | Maier et al. |
| 5,854,008 A | 12/1998 | Diamandis et al. |
| 5,858,676 A | 1/1999 | Yang et al. |
| 5,859,215 A | 1/1999 | Rodriguez-Ubis et al. |
| 5,871,713 A | 2/1999 | Meyer et al. |
| 5,900,228 A | 5/1999 | Meade et al. |
| 5,914,095 A | 6/1999 | Watson |
| 5,955,605 A | 9/1999 | Axworthy et al. |
| 6,030,840 A | 2/2000 | Mullinax et al. |
| 6,045,776 A | 4/2000 | Platzek et al. |
| 6,056,939 A | 5/2000 | Desreux et al. |
| 6,150,520 A | 11/2000 | Argese et al. |
| 6,274,713 B1 | 8/2001 | Sieving et al. |
| 6,670,456 B2 | 12/2003 | Frank et al. |
| 6,709,652 B2 | 3/2004 | Reno et al. |
| RE38,506 E | 4/2004 | Breslow et al. |
| 6,770,261 B2 | 8/2004 | Meade et al. |
| 6,774,228 B1 | 8/2004 | Parker et al. |
| 6,875,419 B2 | 4/2005 | Sherry et al. |
| 6,896,874 B2 | 5/2005 | Li et al. |
| 6,972,122 B2 | 12/2005 | Haroon et al. |
| 2002/0127182 A1 | 9/2002 | Sherry |
| 2002/0136692 A1 | 9/2002 | Haroon |
| 2003/0009976 A1 | 1/2003 | Hauser et al. |
| 2003/0023050 A1 | 1/2003 | Frank |
| 2003/0129579 A1 | 7/2003 | Bornhop |
| 2003/0206865 A1 | 11/2003 | Platzek |
| 2003/0215391 A1 | 11/2003 | Rabito |
| 2004/0067924 A1 | 4/2004 | Frank |
| 2006/0121544 A1* | 6/2006 | Boge et al. ............ 435/7.92 |

OTHER PUBLICATIONS

A. Dadabhoy et al, J. Chem. Soc., Perkin Trans. 2 (2002), pp. 348-357.*

Yu et al., Synthesis of a Europium Complex doe Anion-Sensing Involving Regioselective Substitution of Cylcen, Europ. J. Org. Chem., pp. 4249-4252.

* cited by examiner

LUMINESCENT LANTHANIDE COMPLEXES

CROSS-REFERENCE TO PRIORITY APPLICATIONS

This application is a continuation of PCT Patent Application Ser. No. PCT/US05/35215, filed Sep. 30, 2005, which in turn, is based upon and claims the benefit under 35 U.S.C. § 119(e) of the following U.S. provisional patent applications: Ser. No. 60/615,308, filed Sep. 30, 2004; and Ser. No. 60/683,377, filed May 20, 2005. These three priority applications are each incorporated herein by reference in their entirety for all purposes.

CROSS-REFERENCES TO OTHER MATERIALS

This application also incorporates by reference in their entirety for all purposes the following U.S. provisional patent applications: Ser. No. 60/092,203, filed Jul. 9, 1998; Ser. No. 60/138,311, filed Jun. 9, 1999; Ser. No. 60/138,438, filed Jun. 10, 1999; Ser. No. 60/200,594, filed Apr. 28, 2000; Ser. No. 60/223,642, filed Aug. 8, 2000; Ser. No. 60/241,032, filed Oct. 17, 2000; Ser. No. 60/436,725, filed Dec. 26, 2002; Ser. No. 60/507,006, filed Sep. 29, 2003; Ser. No. 60/507,569, filed Sep. 30, 2003; Ser. No. 60/554,766, filed Mar. 19, 2004; Ser. No. 60/577,079, filed Jun. 4, 2004; Ser. No. 60/602,712, filed Aug. 18, 2004; and Ser. No. 60/615,308, filed Sep. 30, 2004.

This application incorporates by reference in their entirety for all purposes the following U.S. patent applications: Ser. No. 08/929,095, filed Sep. 15, 1997; Ser. No. 09/349,733, filed Jul. 8,1999; Ser. No. 09/596,444, filed Jun. 19, 2000; Ser. No. 09/844,655, filed Apr. 27, 2001; Ser. No. 10/957,332, filed Sep. 30, 2004; Ser. No. 10/746,797, filed Dec. 23, 2004; Ser. No. 11/146,553, filed Jun. 6, 2005; and Ser. No. 11/241,872, filed Sep. 30, 2005.

This application also incorporates by reference in their entirety for all purposes the following PCT patent application: Serial No. PCT/US00/16025, filed Jun. 9, 2000.

This application also incorporates by reference in their entirety for all purposes the various patent applications, patents, and other materials cited elsewhere in the application.

TECHNICAL FIELD

The present teachings relate to luminescent lanthanide chelates, including precursors and derivatives thereof, and their use as detectable labels.

INTRODUCTION

Luminescent and/or colorimetric compositions permit researchers to perform a variety of assays, both qualitative and quantitative, with both sensitivity and accuracy. Lanthanides (or rare earths) are a series of chemically related elements having atomic numbers 58 through 71 in group IIIb of the periodic table. Cations such as trivalent cations of lanthanides may be luminescent, where luminescence refers to emission of light following absorption of light.

The luminescent moiety, or luminophore, may be characterized by a number of parameters, including extinction coefficient, quantum yield, and luminescence lifetime. Extinction coefficient is a wavelength-dependent measure of the absorbing power of a luminophore. Quantum yield is a ratio of the number of photons emitted to the number of photons absorbed by a luminophore. Luminescence lifetime is the average time between absorption and re-emission of light by a luminophore. Lanthanide luminescence is typically exceptional for its long luminescence lifetimes, which often are in the microsecond to millisecond range.

Luminescent lanthanide complexes generally include a luminescent trivalent lanthanide atom and an organic chelator bound to the trivalent lanthanide. The organic chelator may be used to fine-tune the spectral properties of the lanthanide and to permit the lanthanide to participate in specific interactions with biological molecules. The chelator may effectively increase the extinction coefficient of the lanthanide by acting as an "antenna" or "sensitizer" that can absorb light and transfer the associated energy to the lanthanide ion. The chelator also may increase the quantum yield of the lanthanide by decreasing luminescence quenching by the solvent.

The spectral properties of photoluminescence may be characterized by excitation spectrum, emission spectrum, and/or Stokes' shift, among others. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum.

Luminescence-based methods or assays may be influenced by the parameters discussed above—extinction coefficient, quantum yield, luminescence lifetime, excitation and emission spectra, and/or Stokes' shift, among others—and may involve characterizing luminescence intensity (e.g., FLINT), luminescence polarization or anisotropy (e.g., FP), luminescence resonance energy transfer (e.g., FRET), luminescence lifetime (e.g., FLT), total internal reflection luminescence (e.g., TIRF), luminescence correlation spectroscopy (e.g., FCS), and/or luminescence recovery after photobleaching (e.g., FRAP or FPR), among others.

Luminescence methods have several significant potential strengths. For example, luminescence methods may be very sensitive, because modern detectors, such as photomultiplier tubes (PMTs) and charge-coupled devices (CCDs), can detect very low levels of light. In addition, luminescence methods may be very selective, because the luminescence signal may come almost exclusively from the luminophore.

DETAILED DESCRIPTION

The present teachings provide systems, including compositions, kits, and methods, particularly for photoluminescence applications. The compositions and kits may include organic chelators, luminescent lanthanide complexes that incorporate those chelators for use in certain photoluminescence assays, and/or precursors and derivatives of these chelators and complexes, among others. The methods may involve detecting light emitted by the complex, and using properties of that light to understand properties of the complex and its environment. Thus, in this aspect, the compositions may act as reporter molecules, for example, to report on the activity of an enzyme and/or a modulator, such as an agonist or antagonist, of the enzyme.

The organic chelator may be a derivative of a polyazamacrocyclic chelating group. For example, the organic chelator may be a derivative of a 1,4,7,10-tetraazacyclododecane ring system, for example, having the formula:

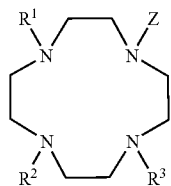

The tetraazacyclododecane chelator may be substituted. For example, the chelator may be substituted at the 1-, 4-, and 7-positions by substituents $R^1$, $R^2$, and $R^3$. The chelator further may be substituted at the 10-position by a sensitizer Z. The sensitizer, as discussed in the Introduction, may act as an antenna that increases luminescence by capturing and transferring light energy to an associated lanthanide. The sensitizer typically comprises a polyheterocyclic ring system.

Substituents $R^1$, $R^2$, and $R^3$, which may be the same or different, may be hydrogen, alkyl having 1-6 carbons, or a substituent selected to facilitate the binding of a lanthanide ion within the tetraazacyclododecane ring. Substituents $R^1$, $R^2$, and $R^3$ typically incorporate functional groups that help complex the selected lanthanide. For example, the $R^1$, $R^2$, and $R^3$ substituents may be further substituted one or more times by hydroxy, alkoxy, amine, carboxyl, ester, amide, or phosphate. The $R^1$, $R^2$, and $R^3$ substituents may be substituted by substituents that themselves incorporate a carbonyl group, such as a carboxylic acid, ester, amide or phosphate. Alternatively or in addition, the $R^1$, $R^2$, and $R^3$ substituents may incorporate a phosphate moiety.

The $R^1$, $R^2$, and $R^3$ substituents are typically acetic acid derivatives, which may be substituted or unsubstituted, as shown below:

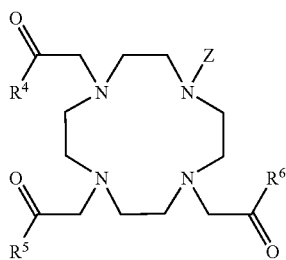

Here, the $R^4$, $R^5$, and $R^6$ substituents may be independently hydroxy, alkyl groups having 1-6 carbons, alkoxy groups having 1-6 carbons, or amine groups, each of which optionally may be further substituted by additional aliphatic groups, aromatic groups, amide groups, and/or heteroatom-substituted aliphatic groups.

The sensitizer Z may comprise a polycyclic heteroaromatic ring system that is bound to the tetraazacyclododecane ring via a covalent linkage. The heteroaromatic ring system may include 2-6 fused aromatic rings, having 1-6 heteroatoms. In some aspects of the chelator, the sensitizer has the formula

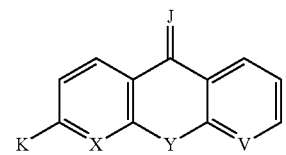

where K is a covalent linkage to the tetraazacyclododecane, and X, Y, V, and J are carbon or a heteroatom that is nitrogen, oxygen, sulfur, or selenium. The sensitizer optionally may be further substituted at one or more positions by additional substituents, such as alkyl, alkoxy, halogen, carboxylic acid, sulfonic acid, and/or phosphate, among others. Typically, the linkage K is an alkyl linkage, and more typically K is a methylene group. In one particular aspect of the chelator, X is nitrogen, V is an aromatic carbon, and both J and Y are oxygen. Particularly preferred sensitizers have the formula

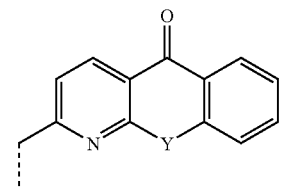

where Y is oxygen, sulfur, or selenium

The chelator typically forms a complex with a lanthanide ion so that at least the nitrogen atoms of the tetraazacyclododecane macrocycle bind to the lanthanide ion. Typically one or more of substituents $R^1$, $R^2$, and $R^3$ also may coordinate with the lanthanide ion, as may a heteroatom present in the sensitizer Z. Where the resulting lanthanide ion is not fully complexed, the remaining coordination sites may be occupied by a solvent molecule, such as water, or by one or more additional ligands that may be strongly coordinated to the lanthanide ion, or may be subject to ligand exchange when the complex is in solution.

The complexed lanthanide ion may be selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Typically, the lanthanide ion is terbium, europium, dysprosium, or samarium. More typically, the lanthanide is terbium.

In a particularly preferred embodiment, the lanthanide complex (including chelator, sensitizer, and lanthanide) has the formula

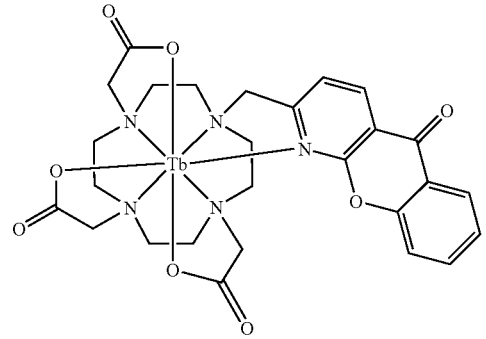

The chelator optionally may be further substituted by one or more reactive functional groups ($R_X$), or conjugated substances ($S_C$), each of which is bound to the chelator via a covalent linking moiety L. The reactive functional group or conjugated substance may be a substituent on the polyazamacrocycle itself, a substituent on $R^1$, $R^2$, or $R^3$, or a substituent on the sensitizer Z. Where the lanthanide complex is substituted by a reactive functional group, it is typically a substituent on the sensitizer moiety.

The covalent linking moiety L is optionally a single covalent bond, such that either the reactive functional group $R_X$ or the conjugated substance $S_C$ is bound directly to the organic chelator. Alternatively, L may incorporate a series of nonhydrogen atoms that form a stable covalent linkage between the reactive functional group or conjugated substance and the chelator. Typically, L may incorporate 1-20 nonhydrogen atoms in a stable conformation. Stable atom conformations include, without limitation, carbon-carbon bonds, amide linkages, ester linkages, sulfonamide linkages, ether linkages, thioether linkages, and/or other covalent bonds. Preferred covalent linkages may include single bonds, carboxamides, sulfonamides, ethers, and carbon-carbon bonds, or a combination thereof.

The reactive functional group $R_X$ may include any functional group that exhibits appropriate reactivity to be conjugated with a desired substance. The choice the reactive group typically depends on the functional groups present on the substance to be conjugated. Typically, functional groups present on such substances include, but are not limited to, alcohols, aldehydes, amines, carboxylic acids, halogens, ketones, phenols, phosphates, and thiols, or a combination thereof. Suitable $R_X$ groups include activated esters of carboxylic acids, aldehydes, alkyl halides, amines, anhydrides, aryl halides, carboxylic acids, haloacetamides, halotriazines, hydrazines (including hydrazides), isocyanates, isothiocyanates, maleimides, phosphoramidites, sulfonyl halides, and thiol groups, or a combination thereof. Typically, $R_X$ is an activated ester of a carboxylic acid, an amine, a haloacetamide, a hydrazine, an isothiocyanate, or a maleimide group. In one aspect of the lanthanide complex, $R_X$ is a succinimidyl ester of a carboxylic acid.

The organic chelators that are substituted with a reactive functional group may be used to prepare a variety of conjugates. The conjugated substance may be a member of a specific binding pair. Alternatively, the conjugated substance may be a molecular carrier. The conjugated substance may include a biomolecule that is an amino acid, a peptide, a protein, a nucleoside, a nucleotide, an oligonucleotide, a nucleic acid polymer, or a carbohydrate. The conjugated substance may include a polar moiety, or a masked polar moiety, or the conjugated substance may include a solid or semi-solid matrix. The conjugated substance may include one or more additional dyes or luminophores.

The conjugated substance $S_C$ may be a naturally occurring or a synthetically modified substance, particularly where it is an amino acid, a peptide, a protein, a nucleoside, a nucleotide, an oligonucleotide, a nucleic acid polymer, or a carbohydrate. For example, the conjugated substance may be a polypeptide or other substance that is naturally or artificially substituted by one or more phosphate functional groups. In this example, the conjugated substance may be substituted by phosphate prior to conjugation with the organic chelator, or the selected conjugated substance may first be conjugated to the organic chelator, and subsequently phosphorylated, for example, by enzymatic phosphorylation.

The conjugated substance $S_C$ also may be a member of a specific binding pair or a molecular carrier. Specific binding pair members typically specifically bind to and are complementary with the complementary member of the specific binding pair. Conjugated members of a specific binding pair can be used to localize compounds of the present teachings to the complementary member of that specific binding pair. Representative specific binding pairs are listed in Table 1.

TABLE 1

| Representative specific binding pair members | |
|---|---|
| antibody | antigen |
| avidin (streptavidin) | biotin |
| DNA | aDNA |
| enzyme | enzyme substrate |
| lectin | carbohydrate |
| receptor | ligand |
| RNA | aRNA |

The conjugated substance $S_C$ may be a biological or artificial polymer, particularly where it is a carrier. Biological polymers include proteins, carbohydrates, and nucleic acid polymers. Artificial polymers include polyethylene glycols and polymeric microparticles composed of polystyrene, latex, or other polymeric material. Preferably, a conjugated carrier is a carbohydrate that is a dextran, or amino-substituted dextran, or a polymer microparticle. The conjugated carrier may be selected so that conjugation of the lanthanide complex to the carrier detectably alters one or more luminescence properties of the complex. In particular, the carrier may be selected so that conjugation of the lanthanide complex to the carrier alters the fluorescence intensity or polarization of the lanthanide complex.

The conjugated substance $S_C$ may be a metal or glass surface, and may be, for example, the sides or bottom of a microwell, or a slide, or the surface of a chip, particularly where the conjugated substance is a solid or semi-solid matrix. The compound of the present teachings is optionally covalently bound to a fiber optic probe, where the probe is composed of glass or functionalized glass (e.g., aminopropyl glass), or the compound is attached to the fiber optic probe via an intermediate polymer, such as polyacrylamide. Incorporation of the compounds of the present teachings on such surfaces permit the remote sensing of sample pH values.

The conjugated substance $S_C$ may include or comprise a dye or luminophore. In such cases, the dye or luminophore may be selected so that energy-transfer occurs between the lanthanide complex and the conjugated dye or luminophore, where the lanthanide complex is optionally the luminescence donor, or the luminescence acceptor.

Further aspects of the present teachings are described in the following sections, including (I) applications; (II) kits, and (III) examples.

I. APPLICATIONS

The lanthanide complexes described herein may be useful as luminescence labels, and are generally utilized by combining a lanthanide complex as described above with the sample of interest under conditions selected to yield a detectable optical response. The term "lanthanide complex" is used herein to refer to all aspects of the described complexes, including, among others, those substituted by reactive functional groups, and/or those associated with conjugated substances, and/or those associated with members of a specific binding pair, and/or those associated with an additional fluorophore or luminophore. The lanthanide complex may form a covalent or non-covalent association or complex with an element of the sample, or may be simply present within the bounds of the sample or portion of the sample. The sample may then be illuminated at a wavelength selected to elicit an optical response. The lanthanide complex is typically added to the sample to determine a specified characteristic of the sample by further comparing the optical response with a standard or expected response.

For biological applications, the lanthanide complex is typically used in an aqueous, mostly aqueous, or aqueous-miscible solution prepared according to methods generally known in the art. The optimal concentration of the lanthanide complex typically is determined by systematic variation until satisfactory results, with minimal background luminescence, are obtained.

The sample of interest may be derived from biological or nonbiological sources. The sample may include a variety of components, such as intact cells, cell extracts, bacteria, viruses, organelles, biomolecules, and mixtures thereof. The lanthanide complex is typically combined with the sample in any way that facilitates contact between the complex and the sample components of interest.

The lanthanide complexes that include conjugated substances may be utilized according to methods well known in the art; e.g., use of antibody conjugates in microscopy and immunofluorescence assays; and nucleotide or oligonucleotide conjugates for nucleic acid hybridization assays and nucleic acid sequencing.

The sample may be illuminated, at any time before, during, and/or after staining, with a wavelength of light selected to give a detectable optical response, and observed with a means for detecting the optical response. A detectable optical response means a change in, or occurrence of, an optical signal that is detectable either by observation or instrumentation. Typically the detectable response is a change in luminescence, such as a change in its intensity, excitation or emission wavelength(s), luminescence lifetime, luminescence polarization, energy transfer, and/or a combination thereof.

The lanthanide complexes described above possess particular utility in luminescence assays involving energy transfer. Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence (and donor lifetime) to decrease and acceptor luminescence to increase (if the acceptor is luminescent). The efficiency of this transfer is very sensitive to the separation R between donor and acceptor, decaying as $1/R^{-6}$. Energy transfer assays use energy transfer to monitor the proximity of donor and acceptor.

One category of energy transfer assay focuses on an increase in energy transfer as donor and acceptor are brought into proximity. This assay may be used to monitor binding, as between two molecules X and Y to form a complex XY, where X and Y interact noncovalently. In such an assay, one molecule may be labeled with a donor D, and the other molecule may be labeled with an acceptor A, such that the interaction between X and Y is not altered appreciably. Independently, D and A may be covalently attached to X and Y, or covalently attached to binding partners of X and Y.

Another category of energy transfer assay focuses on a decrease in energy transfer as donor and acceptor are separated. This assay may be used to monitor cleavage, as by hydrolytic digestion of doubly labeled substrates (peptides, nucleic acids. etc.). In a typical application, two ends of a polypeptide might be labeled with D and A, so that cleavage of the polypeptide by an endopeptidase will separate D and A, and thereby reduce energy transfer.

Energy transfer between D and A may be monitored in various ways. For example, energy transfer may be monitored by observing a resultant decrease in the emission intensity of D and increase in the emission intensity of A (if A is a luminophore). Energy transfer also may be monitored by observing a resultant change in lifetime (e.g., a decrease in the lifetime of D).

In a preferred assay, a long-lifetime luminescent lanthanide complex as described above will be used as a donor, and a short-lifetime luminophore will be used as an acceptor. The donor will be excited using a flash of light having a wavelength near the excitation maximum of D. Next, there will be a brief wait, so that electronic transients and/or short-lifetime background luminescence are permitted to decay. Subsequently, donor and/or acceptor luminescence intensity can be detected and optionally integrated. Donor luminescence will be reduced if there is energy transfer, and acceptor luminescence will be observed only if there is energy transfer.

The disclosed lanthanide complexes have particular utility in assays that are intended to detect or quantify molecular modification of an assay component, for example, as described in the following patent applications, which are incorporated herein by reference in their entireties for all purposes: (1) U.S. patent application Ser. No. 10/746,797, filed Dec. 23, 2003; and (2) U.S. Provisional Patent Application Ser. No. 60/615,308, filed Sep. 30, 2004. These assays may incorporate one or more steps, including (a) contacting at least one member of a pair of molecules or other entities related by a molecular modification with a binding partner capable of binding one of the pair of molecules but not the other, (b) detecting a response indicative of the extent of binding between the at least one member of the pair and the binding partner, and (c) correlating the response with the extent of modification, or with the activity of an enzyme that affects the modification. The extent of binding or modification, or the activity, as used herein, is intended to include the presence or absence of binding or modification, and the presence or absence of activity. The assays further may include contacting the at least one member with the enzyme before and/or after the steps of contacting, detecting, and correlating. The assays further may include contacting the at least one member and the enzyme with a candidate compound such as a putative modulator before and/or after the step of contacting the at least one member with the enzyme, and determining the ability of the candidate compound to promote or inhibit the modification by its effects on the extent of binding. Alternatively, or in addition, the assays further may include washing the sample including the at least one member and the binding partner to remove any member of the pair not bound to the binding partner prior to the step of detecting the extent of binding. In some embodiments, the assays may include repeating the steps of contacting, detecting, and/or correlating for the same sample and/or a plurality of different samples. For example, the assays may involve providing a sample holder having a plurality of sample sites supporting a corresponding plurality of samples, and sequentially and/or simultaneously repeating the steps of contacting, detecting, and/or correlating for the plurality of samples. The remainder of this section describes in more detail the steps of (a) contacting, (b) detecting, and (c) correlating.

(A) Contacting. The step of contacting assay components such as enzymes, enzyme modulators, substrates, products, and/or binding partners with one another and/or with other species generally comprises any method for bringing any specified combination of these components into functional and/or reactive contact. A preferred method is by mixing and/or forming the materials in solution, although other methods, such as attaching one or more components such as the binding partner to a bead or surface, also may be used, as long as the components retain at least some function, specificity, and/or binding affinity following such attachment. Exemplary apparatus having fluidics capability suitable for contacting or otherwise preparing assay components are described in the following U.S. patent applications, which are incorporated herein by reference: Ser. No. 09/777,343, filed Feb. 5, 2001; and Ser. No. 10/061,416, filed Feb. 1, 2002.

One or more of the assay components may comprise a sample, which typically takes the form of a solution containing one or more biomolecules that are biological and/or synthetic in origin. The sample may be a biological sample that is prepared from a blood sample, a urine sample, a swipe, or a smear, among others. Alternatively, the sample may be an environmental sample that is prepared from an air sample, a water sample, or a soil sample, among others. The sample typically is aqueous but may contain biologically compatible organic solvents, buffering agents, inorganic salts, and/or other components known in the art for assay solutions.

The assay components and/or sample may be supported for contact and/or analysis by any substrate or material capable of providing such support. Suitable substrates may include microplates, PCR plates, biochips, and hybridization chambers, among others, where features such as microplate wells and microarray (i.e., biochip) sites may comprise assay sites. Suitable microplates are described in the following U.S. patent applications, which are incorporated herein by reference: Ser. No. 08/840,553, filed Apr. 14, 1997, now abandoned; and Ser. No. 09/478,819, filed Jan. 5, 2000, now U.S. Pat. No. 6,488,892. These microplates may include 96, 384, 1536, or other numbers of wells. These microplates also may include wells having small (~50 mL) volumes, elevated bottoms, and/or frusto-conical shapes capable of matching a sensed volume. Suitable PCR plates may include the same (or a similar) footprint, well spacing, and well shape as the preferred microplates, while possessing stiffness adequate for automated handling and thermal stability adequate for PCR. Suitable microarrays include nucleic acid and polypeptide microarrays, which are described in Bob Sinclair, Everything's Great When It Sits on a Chip: A Bright Future for DNA Arrays, 13 THE SCIENTIST, May 24, 1999, at 18, which is incorporated herein by reference: Suitable hybridization chambers are described in U.S. Pat. No. 6,486,947, issued Nov. 26, 2002, which is incorporated herein by reference.

(B) Detecting. The step of detecting a response indicative of the extent of binding generally comprises any method for effectuating such detection, including detecting and/or quantifying a change in, or an occurrence of, a suitable parameter and/or signal. The method may include luminescence and/or nonluminescence methods, and heterogeneous and/or homogeneous methods, among others.

Luminescence and nonluminescence methods may be distinguished by whether they involve detection of light emitted by a component of the sample. Luminescence assays involve detecting light emitted by a luminescent compound (or luminophore) and using properties of that light to understand properties of the compound and its environment. A typical luminescence assay may involve (1) exposing a sample to a condition capable of inducing luminescence from the sample, and (2) measuring a detectable luminescence response indicative of the extent of binding between the member of interest and a corresponding binding partner. Most luminescence assays are based on photoluminescence, which is luminescence emitted in response to absorption of suitable excitation light. However, luminescence assays also may be based on chemiluminescence, which is luminescence emitted in response to chemical excitation, and electrochemiluminescence, which is luminescence emitted in response to electrochemical energy. Suitable luminescence assays include, among others, (1) luminescence intensity, which involves detection of the intensity of luminescence, (2) luminescence polarization, which involves detection of the polarization of light emitted in response to excitation by polarized light, and (3) luminescence energy transfer. Luminescence energy transfer involves detection of energy transfer between a luminescent donor and a suitable acceptor (a donor-acceptor energy transfer pair). Such energy transfer may occur with or without the emission of a photon. Generally the efficiency of the energy transfer is dependent on the distance between the donor and acceptor. Accordingly, the amount of energy transfer detected relates, at least partially, to the proximity of the energy donor and acceptor, and thus may be correlated with conversion of substrate to product in an assay. In particular, the energy donor and acceptor may be placed in (or out of) proximity by the enzyme reaction itself, or by selective association of a substrate or product of the enzyme with an association partner. Nonluminescence assays involve using a detectable response other than light emitted by the sample, such as absorption, scattering, and/or radioactivity, among others. These and other nonluminescence assays are described in the following materials, which are incorporated herein by reference: U.S. Pat. No. 6,466,316, issued Oct. 15, 2002; and Joseph R. Lakowicz, Principles of Fluorescence Spectroscopy (2nd ed. 1999).

The detectable luminescence response generally comprises a change in, or an occurrence of, a luminescence signal that is detectable by direct visual observation and/or by suitable instrumentation. Typically, the detectable response is a change in a property of the luminescence, such as a change in the intensity, polarization, energy transfer, lifetime, and/or excitation or emission wavelength distribution of the luminescence. For example, energy transfer may be measured as a decrease in donor luminescence, an increase (often from zero) in acceptor luminescence, and/or a decrease in donor luminescence lifetime, among others. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence assays, the detectable response may be generated directly using a luminophore associated with an assay component actually involved in binding such as A* or BP, or indirectly using a luminophore associated with another (e.g., reporter or indicator) component. Suitable methods and luminophores for luminescently labeling assay components are described in the following materials, which are incorporated herein by reference: Richard P. Haugland, Handbook of Fluorescent Probes and Research Chemicals (6th ed. 1996); U.S. patent application Ser. No. 09/813,107, filed Mar. 19, 2001; and U.S. patent application Ser. No. 09/815,932, filed Mar. 23, 2001.

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a trivalent metal or other suitable binding partner. Such metals may include gallium (Ga, including Ga(III)), iron (Fe), aluminum (Al), and/or zinc (Zn), among others. Suitable metals and other binding partners are described in more detail in U.S. patent application Ser. No. 10/746,797, filed Dec. 23, 2003, which is incorporated herein by reference. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a luminescence response that is affected in some way by binding or unbinding of bound and unbound species without separating the bound and unbound species. Alternatively, or in addition, enzyme activity may result in increased or decreased energy transfer between a donor and acceptor of an energy transfer pair, based on whether the acceptor quenches or not, and based on whether enzyme activity in the assay results in increased or decreased proximity of the donor and acceptor. Homogeneous assays typically are simpler to perform but more complicated to develop than heterogeneous assays.

response (e.g., derived from a similar measurement of the same sample at a different time and/or another sample at any time) and/or a calibration standard (e.g., derived from a calibration curve, a calculation of an expected response, and/or a luminescent reference material). Thus, for example, in a energy transfer assay for cyclic nucleotide concentration, the cyclic nucleotide concentration in an unknown sample may be determined by matching the energy transfer efficiency measured for the unknown with the cyclic nucleotide concentration corresponding to that efficiency in a calibration curve generated under similar conditions by measuring energy transfer efficiency as a function of cyclic nucleotide concentration. More generally, the following table shows representative qualitative changes in the indicated detectable luminescence response upon binding between A* and BP following a forward reaction A→A*.

TABLE 2

| Label on A* | Label on BP | Intensity (Luminophore) | Intensity (Acceptor) | FP (Luminophore) | ET (Lum.→Acc.) |
|---|---|---|---|---|---|
| Luminophore | — | | | Increases | |
| — | Luminophore | | | Increases | |
| Luminophore | Quencher | Decreases | | | |
| Quencher | Luminophore | Decreases | | | |
| Luminophore | Acceptor | Decreases | Increases | Decreases | Increases |
| Acceptor | Luminophore | Decreases | Increases | | Increases |

This reaction is representative of a phosphorylation reaction performed by a kinase or a decyclization reaction performed by a PDE, assuming that the binding partner binds to the (noncyclized) phosphorylated species. Similarly, the following table shows representative qualitative changes in the indicated detectable luminescence response upon binding of A* and BP following the reverse reaction A*→A.

TABLE 3

| Label on A* | Label on BP | Intensity (Luminophore) | Intensity (Acceptor) | FP (Luminophore) | ET (Lum. → Acc.) |
|---|---|---|---|---|---|
| Luminophore | — | | | Decreases | |
| — | Luminophore | | | Decreases | |
| Luminophore | Quencher | Increases | | | |
| Quencher | Luminophore | Increases | | | |
| Luminophore | Acceptor | Increases | Decreases | Increases | Decreases |
| Acceptor | Luminophore | Increases | Decreases | | Decreases |

(C) Correlating. The step of correlating generally comprises any method for correlating the extent of binding with the extent of modification of the assay component being analyzed, and/or with the presence and/or activity of an enzyme that affects the modification. The nature of this step depends in part on whether the detectable response is simply detected or whether it is quantified. If the response is simply detected, it typically will be used to evaluate the presence of a component such as a substrate, product, and/or enzyme, or the presence of an activity such as an enzyme or modulator activity. In contrast, if the response is quantified, it typically will be used to evaluate the presence and/or quantity of a component such as a substrate, product, and/or enzyme, or the presence and/or activity of a component such as an enzyme or modulator.

The correlation generally may be performed by comparing the presence and/or magnitude of the response to another This reaction is representative of a dephosphorylation reaction performed by a phosphatase or a cyclization reaction performed by a cyclase, assuming again that the binding partner binds to the (noncyclized) phosphorylated species.

The assays of the present teachings optionally may be performed using various apparatus that include luminescence detectors and sample holders such as microplates, among others. The methods include photoluminescence methods, such as fluorescence intensity, among others. The compositions include various energy transfer donors and acceptors, among others.

II. KITS

The lanthanide complexes disclosed herein may be provided in the form of kits for general use, or optionally formulated for performing selected assays. These kits may include the organic chelator, or the lanthanide complex, or both. The kit may optionally include chemically reactive forms of the chelator or complex to permit a user to label substances of interest and develop individual assays. Alternatively, the kits may include selected conjugates of the complex specifically for use in a particular assay, such as where the conjugated substance is a member of a specific binding pair. The kit optionally incorporates additional reagents, including but not limited to buffering agents, luminescence calibration standards, enzymes, enzyme substrates, nucleic acid stains, labeled antibodies, and/or other additional luminescence detection reagents. The lanthanide complexes are optionally present in pure form, or as a concentrated stock solution, or in a prediluted solution ready for use in the appropriate assay. The kit may be designed for use in an automated and/or high-throughput assay, and therefore compatible with use in conjunction with microplate readers, microfluidic methods, and/or other automated high-throughput methods.

III. EXAMPLES

The following examples describe selected aspects and embodiments of the present teachings. These examples are included for illustration and are not intended to limit or define the entire scope of the present teachings.

Example 1

The structures of two examples of lanthanide complexes, DP-1 and DP-2, are provided below. These complexes include a terbium ion, a heteropolycyclic sensitizer moiety, and are efficiently excited by light having a wavelength of about 320 to about 390 nm.

DP-1

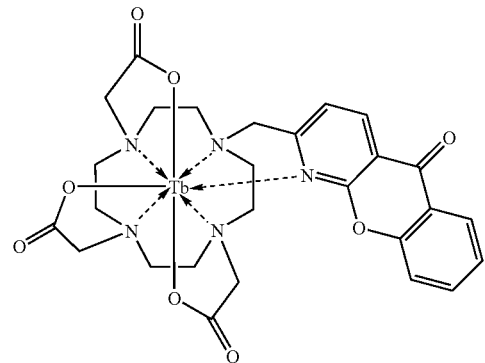

DP-2

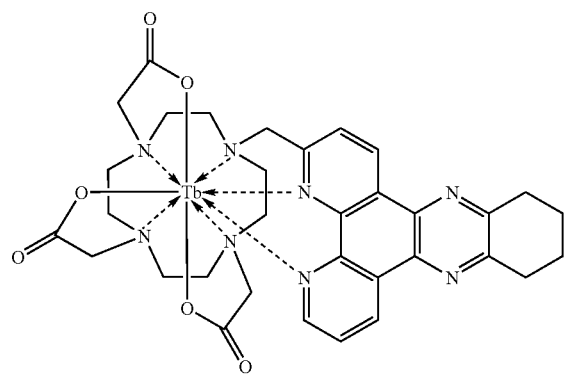

Analogs of the DP-1 and DP-2 complexes may be prepared using other lanthanides, for example Eu, Dy, and Sm, among others. The DP-1 and DP-2 complexes are generally useful as luminescent labels, and particularly useful when used as reporter molecules in experiments based on Time-Resolved Fluorescence Resonance Energy Transfer (TR-FRET).

Example 2

As discussed above, selected lanthanide complexes may be prepared that include reactive functional groups. The presence of a reactive group ($R_x$) permits the covalent attachment of substances having desired biochemical properties to form conjugates. In one aspect, the conjugates substance may be a peptides or other organic ligand that is itself substituted by one or more phosphate groups. For example, selected complexes derived from DP-1 are provided below:

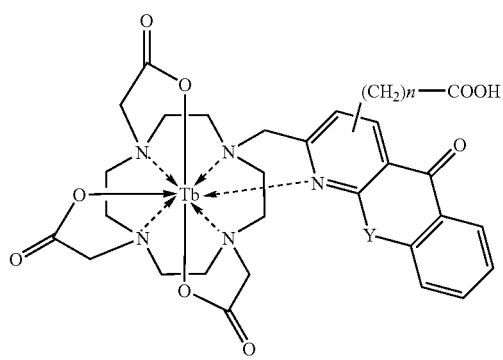
(1)

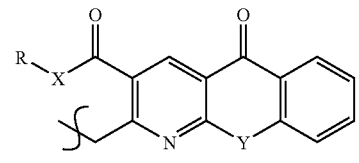
(1a)

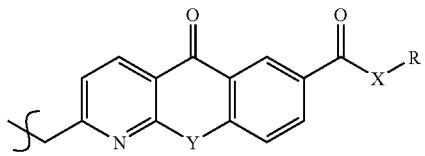
(1b)

In compound (1) above, n=0 to about 5; X=O, NH, or S; Y=O, S, or Se. The covalent linkage (i.e., —$(CH_2)_n$—COOH) can be attached to the complex at the 3-through 8-position of the sensitizer moiety. The heteroatom Y on the sensitizer may be oxygen, sulfur, or selenium. Selected specific examples of reactive group-substituted sensitizer groups are shown in structures (1a) and (1b), specifically where the sensitizer is derivatized at the 3-position (1a), or at the 6-position (1b).

A carboxyl group may be attached to the sensitizer moiety, which is then reacted with an amine group on a peptide or other organic molecule containing phosphate, as shown in structures 1a and 1b above. Alternatively, structure 1 may be reacted with an alcohol or thiol to form an ester or thioester. R may be a peptide containing one or more amino acid residues including phosphoserine, phosphothreonine or phosphotyrosine. More specifically, R may be a phosphoPKAtide. Alternatively, R can be an organic compound containing one or more phosphate groups, including but not limited to alkylphosphates, alkyldiphosphates, alkyltriphosphates, or aryl moieties containing one or more phosphate groups.

Example 3

In structure (2) below, the sensitizer moiety has been derivatized with an isothiocyanate group that can then react with an amine to form a covalent thiourea linkage.

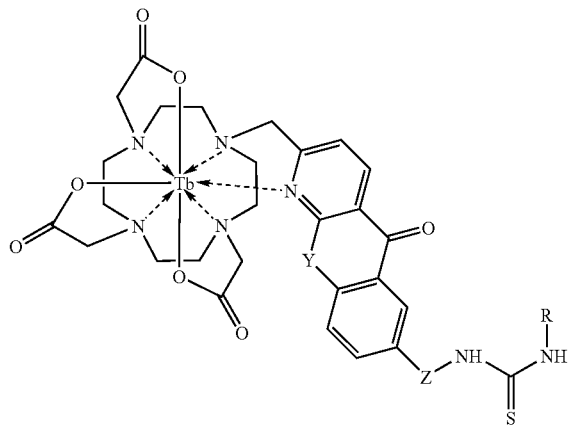
(2)

In compound (2) above, Y can be O or S; Z=none or an alkylphenyl linker. The covalent linkage (i.e., —Z-NH—) can be at the 3-through 8-position of the aromatic sensitizer. The R group may be a peptide containing one or more amino acid residues, including for example phosphoserine, phosphothreonine or phosphotyrosine. More particularly, the R group can be phosphoPKAtide. Alternatively, R can be any organic compound that includes one or more phosphate groups, including but not limited to alkylphosphate, alkyldiphosphate or alkyltriphosphate, or aryl moieties containing one or more phosphate groups.

Example 4

The DP-2 complex may be derivatized with one or more reactive functional groups, as shown below.

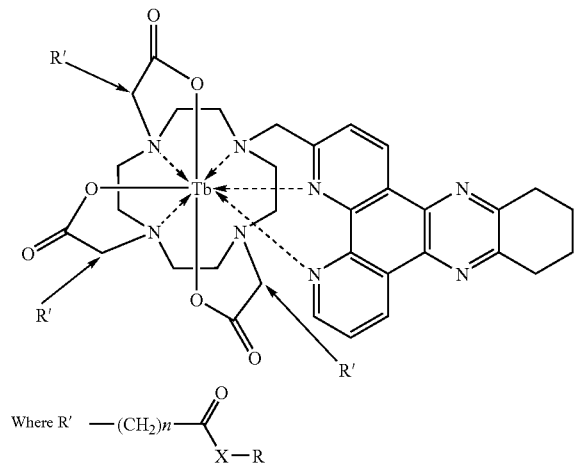

In the above structure, n=1 through about 5, X is NH, O, or S. The position of the covalent linkage (i.e., —(CH$_2$)$_n$—), can be on either available carbon atom of the acetate sidechains on the polyazamacrocycle. R can be a peptide containing one or more amino acid residues from among the following: phosphoserine, phosphothreonine or phosphotyrosine. More particularly, R can be phosphoPKAtide. Alternatively, R can be any organic compound containing one or more phosphate groups, e.g., an alkylphosphate, alkyldiphosphate or alkyltriphosphate, or aryl moieties containing one or more phosphate groups.

Example 5

Additional chemically reactive versions of the complexes DP-1 and DP-2 may be prepared, particularly where the covalent linkage is located at any position on either the sensitizer moiety or the organic chelator. In particular, derivatives may be prepared where the lanthanide complex is substituted by a reactive functional group suitable for covalent coupling to form a desired conjugate. Selected reactive functional groups include, isothiocyanate, activated carboxylic acid esters, acid chlorides, sulfhydryl, phenols, maleimides, and others known to those skilled in the art of bioconjugate chemistry. Further the lanthanide may be any lanthanide ion that confers luminescence on the resulting complex, for example Tb, Eu, Sm, Dy. Such complexes would be generally useful as luminescent labels for applications involving TR-FRET.

The disclosure set forth above may encompass multiple distinct inventions with independent utility. The disclosure includes a number of section headings, which were added for convenience, and which are not intended to limit the disclosure in any way (e.g., the headings to not foreclose using information described in one section in place of, and/or in combination with, information described in other sections). Similarly, the disclosure relates information regarding specific embodiments, which are included for illustrative purposes, and which are not to be considered in a limiting sense, because numerous variations are possible. The inventive subject matter of the disclosure includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A luminophore comprising a chelator, a polycyclic heteroaromatic sensitizer moiety, and a lanthanide, the luminophore having the formula

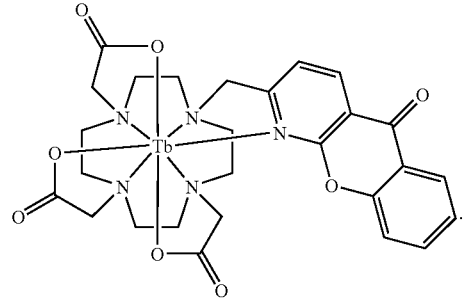

2. The luminophore of claim 1, where the luminophore is further substituted by one or more reactive functional groups or conjugated substances.

3. The luminophore of claim 2, where each reactive functional group or conjugated substance is independently bound to the luminophore via a covalent linking moiety.

4. The luminophore of claim 2 where the reactive functional group or conjugated substance is a substituent on the polycyclic heteroaromatic sensitizer moiety.

5. The luminophore of claim 2, where the conjugated substance is a member of a specific binding pair.

6. The luminophore of claim 3, where at least one of the covalent linking moieties includes a linkage metal.

7. The luminophore of claim 6, where at least one of the covalent linking moieties includes a metal-binding functional group that binds to the linkage metal.

8. The luminophore of claim 7, where the metal-binding functional group is a phosphate, sulfonic acid, or carboxylic acid functional group.

9. The luminophore of claim 6, where the linkage metal is aluminum, iron, or gallium.

10. The luminophore of claim 7, where the metal-binding functional group is a phosphate functional group, and the linkage metal is gallium(III).

11. A method of staining a sample, comprising:
combining a luminophore according to claim 1 with the sample; and
illuminating the combined sample under conditions that elicit an optical response from the luminophore.

12. The method of claim 11, further comprising comparing the optical response with a standard or expected response.

13. The method of claim 11, where the luminophore is further substituted by one or more reactive functional groups or conjugated substances.

14. The method of claim 13, where each reactive functional group or conjugated substance is bound to the luminophore via a covalent linking moiety.

15. The method of claim 14 where the reactive functional group or conjugated substance is a substituent on the polycyclic heteroaromatic sensitizer moiety.

16. The method of claim 13, where the conjugated substance is a member of a specific binding pair.

17. The method of claim 11 further comprising bringing the sample into contact with an energy transfer donor or an energy transfer acceptor capable of participating in luminescence energy transfer with the luminophore.

18. The method of claim 17, where the sample is brought into contact with an energy transfer acceptor capable of accepting energy transfer from the luminophore.

19. The luminophore of claim 4, where the polycyclic heteroaromatic sensitizer moiety is further substituted at one or more positions by alkyl, alkoxy, halogen, carboxylic acid, sulfonic acid, or phosphonate.

20. A luminophore comprising a chelator, a lanthanide ion, and a sensitizer moiety, the luminophore having the formula

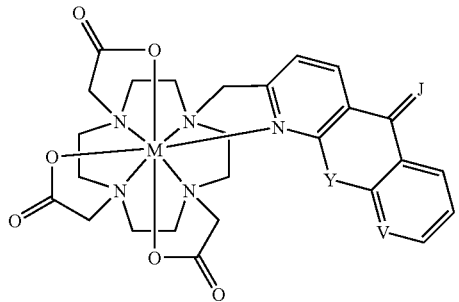

where M is a complexed lanthanide metal; J is oxygen, sulfur, or selenium; Y is oxygen, sulfur, or selenium; V is carbon or nitrogen; and the luminophore is optionally further substituted by one or more reactive functional groups, conjugated substances, alkyl, alkoxy, halogen, carboxylic acid, sulfonic acid, or phosphonate moieties.

21. The luminophore of claim 20, where the sensitizer moiety is further substituted at one or more positions by alkyl, alkoxy, halogen, carboxylic acid, sulfonic acid, or phosphonate.

22. The luminophore of claim 20, where the complexed lanthanide metal M is selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

23. The luminophore of claim 22, where the complexed lanthanide metal M is selected from terbium, europium, dysprosium, and samarium.

24. The luminophore of claim 22, where the complexed lanthanide metal M is terbium.

25. The luminophore of claim 20, where the luminophore is further substituted by one or more reactive functional groups or conjugated substances.

26. A method of staining a sample, comprising:
combining a luminophore according to claim 20 with the sample; and
illuminating the sample under conditions that elicit an optical response.

* * * * *